United States Patent
Moore

(10) Patent No.: US 7,795,293 B2
(45) Date of Patent: *Sep. 14, 2010

(54) 3'-[(2Z)-[1-(3,4-DIMETHYLPHENYL)-1,5-DIHYDRO-3-METHYL-5-OXO-4H-PYRAZOL-4-YLIDENE]HYDRAZINO]-2'-HYDROXY-[1,1'-BIPHENYL]-3-CARBOXYLIC ACID BIS-(MONOETHANOLAMINE)

(75) Inventor: Stephen Moore, Tonbridge (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/472,819

(22) Filed: May 27, 2009

(65) Prior Publication Data

US 2009/0291995 A1 Nov. 26, 2009

Related U.S. Application Data

(63) Continuation of application No. 10/515,304, filed as application No. PCT/US03/16255 on May 21, 2003, now Pat. No. 7,547,719.

(60) Provisional application No. 60/382,871, filed on May 22, 2002.

(51) Int. Cl.
A61K 31/4152 (2006.01)
C07D 231/38 (2006.01)

(52) U.S. Cl. .................... 514/404; 548/367.4

(58) Field of Classification Search ............... 514/404; 548/367.4

See application file for complete search history.

(56) References Cited

U.S. PATENT DOCUMENTS

| | | | |
|---|---|---|---|
| 851,444 A | 4/1907 | Shulthess | |
| 2,809,963 A | 10/1957 | Hanhart | 534/665 |
| 2,950,273 A | 8/1960 | Pelz | |
| 3,366,619 A | 1/1968 | DeLucia | |
| 4,435,417 A | 3/1984 | Toja et al. | |
| 4,510,149 A | 4/1985 | Cozzi et al. | |
| 4,582,831 A | 4/1986 | Robertson | |
| 4,686,285 A | 8/1987 | Pedrazzi | 534/606 |
| 4,880,788 A | 11/1989 | Moake et al. | |
| 4,948,900 A | 8/1990 | Iijima et al. | |
| 5,326,776 A | 7/1994 | Winn et al. | |
| 5,482,546 A | 1/1996 | Eida et al. | |
| 5,532,202 A | 7/1996 | Yoshida | |
| 5,622,818 A | 4/1997 | Kapp et al. | |
| 5,669,967 A | 9/1997 | Hays | |
| 5,746,821 A | 5/1998 | Hays | |
| 5,760,038 A | 6/1998 | Murugesan et al. | |
| 5,932,546 A | 8/1999 | Barrett et al. | |
| 6,214,813 B1 | 4/2001 | Zhang et al. | |
| 6,238,442 B1 | 5/2001 | Schumacher et al. | |
| 6,248,871 B1 | 6/2001 | Ebenezer et al. | |
| 6,280,959 B1 | 8/2001 | Gleason et al. | |
| 6,436,915 B1 | 8/2002 | Zhang et al. | |
| 7,160,870 B2 | 1/2007 | Duffy et al. | |
| 2003/0060453 A1 | 3/2003 | Zhang et al. | |
| 2004/0063764 A1 | 4/2004 | Takemoto et al. | |
| 2004/0082626 A1 | 4/2004 | Takemoto et al. | |

FOREIGN PATENT DOCUMENTS

| | | |
|---|---|---|
| DE | 193350 | 11/1904 |
| DE | 193350 | 12/1907 |
| DE | 1046220 | 12/1958 |
| EP | 0 638 617 | 8/1994 |
| EP | 1 207 155 | 7/2000 |
| EP | 1 253 142 | 1/2001 |
| EP | 1 104 674 | 6/2001 |
| EP | 1 104 674 | 8/2001 |
| GB | 826207 | 7/1956 |
| GB | 779 880 | 7/1957 |
| JP | 2002-371213 | 12/2002 |
| WO | WO 93/17681 | 9/1993 |
| WO | WO 94/26709 | 11/1994 |
| WO | WO 96/40750 | 12/1996 |
| WO | WO 98/46606 | 10/1998 |
| WO | WO 99/11262 | 3/1999 |
| WO | WO 99/15500 | 4/1999 |
| WO | WO 00/35446 | 6/2000 |
| WO | WO 00/68222 | 11/2000 |
| WO | WO 01/77080 | 1/2001 |
| WO | WO 01/07423 | 2/2001 |
| WO | WO 01/17349 | 3/2001 |
| WO | WO 01/21180 | 3/2001 |
| WO | WO 01/34585 | 5/2001 |
| WO | WO 01/77108 | 10/2001 |

(Continued)

OTHER PUBLICATIONS

Yamazaki, et al., Database HCAPLUS, AN 1995: Abstract, 196968.

(Continued)

*Primary Examiner*—Rebecca L Anderson
*Assistant Examiner*—Jason M Nolan
(74) *Attorney, Agent, or Firm*—Wayne J. Dustman; Edward R. Gimmi

(57) ABSTRACT

An improved thrombopoietin mimetic, the bis-(monoethanolamine) salt of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid.

3 Claims, No Drawings

FOREIGN PATENT DOCUMENTS

| WO | WO 01/89457 | 11/2001 |
|---|---|---|
| WO | WO 02/39099 | 1/2002 |
| WO | WO 02/59100 | 1/2002 |
| WO | WO 02/49413 | 6/2002 |
| WO | WO 02/057300 | 7/2002 |
| WO | WO 02/085343 | 10/2002 |
| WO | WO 03/103686 | 12/2002 |
| WO | WO 03/045379 | 6/2003 |
| WO | WO03/074550 | 9/2003 |
| WO | WO03/098992 | 12/2003 |
| WO | WO 2004/054515 | 7/2004 |
| WO | WO 2004/096154 | 11/2004 |
| WO | WO 2005/041867 | 5/2005 |

OTHER PUBLICATIONS

A. Esteve, Ann. Pharm. Franc., 1950, vol. 8, No. 9-10, pp. 594-604.
Morris, et al., Anti-Cancer Drugs, 1997, vol. 8, No. 8, pp. 746-755.
Duffy, et al., J. Med. Chem., 2001, vol. 44, No. 22, Abstract No. XP002197261.
Bartley, et al., Cell, 1994, vol. 77, pp. 1117-1124.
Olszewski, et al., Database CAPLUS on STN, 1995, Chem. Abstracts, No. 122:81695.
Olszewski, et al., J. Org. Chem., 1994, vol. 59, pp. 4285-4296.
CAS online Registry No. 496775-62-3, Mar. 2002.
Lamb, et al., Nucleic Acids Research, 1995, vol. 23, No. 16, pp. 3283-3289.
Seidel, et al., Proc. Natl. Acad. Sci. USA, Mar. 1995, vol. 92, pp. 3041-3045.
Berkhout, et al., J. of Biological Chemistry, Jun. 1997, vol. 272, No. 26, pp. 16404-16413.
Vermeulen, et al., Blood, 1998, vol. 92, No. 3, pp. 894-900.
Hasegawa, et al., Int. J. Immunopharmac, 1996, vol. 18, No. 2, pp. 103-112.
Kumamoto, et al., British Journal of Haematology, 1999, vol. 105, pp. 1025-1033.
Shiotsu, et al., Experimental Hematology, 1998, vol. 26, pp. 1195-1201.
Komatsu, et al., Blood, 1996, vol. 87, No. 11, pp. 4552-4560.
Uguccioni, et al., J. Exp. Med., 1996, vol. 183, pp. 2397-2384.
Taylor, et al., J. Org. Chem., 1987, vol. 52, pp. 4107-4110.
Kuter, et al., Seminars in Hematology, Apr. 2000, vol. 37, No. 2, pp. 41-49.
Ballestrero, et al., Oncology, 2000, vol. 59, pp. 7-13.
Sawai, et al., Journal of Leukocyte Biology, Jul. 2000, vol. 68, pp. 137-143.
Vigon, et al., Proc. Natl. Acad. Sci. USA, Jun. 1992, vol. 89, pp. 5640-5644.
Laurenz, et al., Comp. Biochem Physiol., 1997, vol. 116A, No. 4, pp. 369-377.
Metcalf, et al., Nature, Jun. 16, 1994, vol. 369, pp. 519-520.
Bussel, et al., Seminars in Hematology, 2000, vol. 37, pp. 1-49 (Table of Contents).
McDonald, et al., Am. J. of Pediatric Hematology/Oncology, 1992, vol. 14, No. 1, pp. 8-21.
Souyri, et al., Cell, 1990, vol. 63, pp. 1137-1147.
Bazan, et al., Pro. Natl. Acad. Sci. USA, Sep. 1990, vol. 87, pp. 6934-6938.
Sauvage, et al., Nature, Jun. 16, 1994, vol. 369, pp. 533-538.
Wendling, et al., Nature, Jun. 16, 1994, vol. 369, pp. 571-574.
Kaushansky, et al., Nature, Jun. 16, 1994, vol. 369, pp. 568-571.
King, et al., The Journal of Immunology, 2000, pp. 3774-3782.
Kikuta, et al., Experimental Hematology, 2000, vol. 28, pp. 311-317.
Somlo, et al., Blood, May 1, 1992, vol. 93, No. 9, pp. 2798-2806.
Kirley-Neumann, et al., Cytokines, Cellular & Molecular Therapy, 2000, vol. 6, pp. 47-56.
Egger, et al., Bone Marrow Transplant, 1998, vol. 22, pp. 34-35.
Gaudron, et al., Stem Cells, 1999, vol. 17, pp. 100-106.
Fetscher, et al., Current Opinion in Hematology, 2000, vol. 7, pp. 255-260.
Clemons, et al., Breast Cancer Res. Treatment, 1999, vol. 57, pp. 127.
Greene, "Protective Groups in Organic Synthesis", 1981, Table of Contents.
Methia, et al., Blood, 1993, vol. 82, No. 5, pp. 1395-1401.
Yamazaki, et al., Japn. J. Toxicol. Environ. Health, 1994, vol. 94, No. 5, pp. 448-453.
Duffin, et al., J. of the Chem. Soc., 1954, pp. 408-441.
King, et al., Scand. J. of Immunol., 1999, vol. 49, No. 2, pp. 184-192.
Konica Corp. Derwent No. 92-077508/10, 1992.
Mitsubishi Pharma Corp. Derwent No. 2003-845201/78, 2003.
Mitsubishi Pharma Corp. Derwent No. 2003-767492/72, 2003.
Balli, et al., Dyes. Pigm., 1981, vol. 2, No. 2, pp. 93-124.
Balli, et al., Justus Liebigs Ann. Chem., 1966, vol. 699, pp. 133-134.
Dziomko, et al., Chem. Heterocycl. Compd., 1984, vol. 20, No. 2, pp. 196-200.
Duffy, et al., J. Med. Chem., 2001, vol. 44, No. 22, p. 3730-3745.
Kimura, et al., FEBS Letters, 1998, vol. 428, No. 3, pp. 250-254.
Beckert, et al., Monatshefte Fur Chemie, 1989, vol. 120, pp. 1125-1137.
A. Esteve, Ann. Pharm. Franc., 1950, vol. 8, No. 9-10.
PCT/US2004/13468 filed Apr. 29, 2004. (WO 04/096154).
PCT/US2004/034944 filed Oct. 21, 2004. (WO 05/041867).
Minssen-Guette, et al., Bulletin De La Societe Chimique De France, 1986, No. 5, pp. 2106-2110.
European Search report dated Dec. 15, 2003.
European office action dated Feb. 2, 2005.
Bussel, et al., Seminars in Hematology, 2000, vol. 37, pp. 1-49 (whole journal). see ids #7.
Balli, et al., Dyes. Pigm., 1981, vol. 2, No. 2, pp. 93-124 (sent original).
Balli, et al., Justus Liebigs Ann. Chem., 1966, vol. 699, pp. 133-144. (sent original).
People's Republic of China, Office Action, dated Mar. 17, 2006.

3'-[(2Z)-[1-(3,4-DIMETHYLPHENYL)-1,5-DIHYDRO-3-METHYL-5-OXO-4H-PYRAZOL-4-YLIDENE]HYDRAZINO]-2'-HYDROXY-[1,1'-BIPHENYL]-3-CARBOXYLIC ACID BIS-(MONOETHANOLAMINE)

This application is a continuation of U.S. application Ser. No. 10/515,304, filed Feb. 22, 2006, now U.S. Pat. No. 7,547,719, which is a 371 of International Application No. PCT/US03/016255, filed May 21, 2003, which claims the benefit of U.S. Provisional Application No. 60/382,871, filed May 22, 2002.

This invention relates to an improved thrombopoietin (hereinafter TPO) mimetic, the bis-(monoethanolamine) salt of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid. The compound is represented by Structure I:

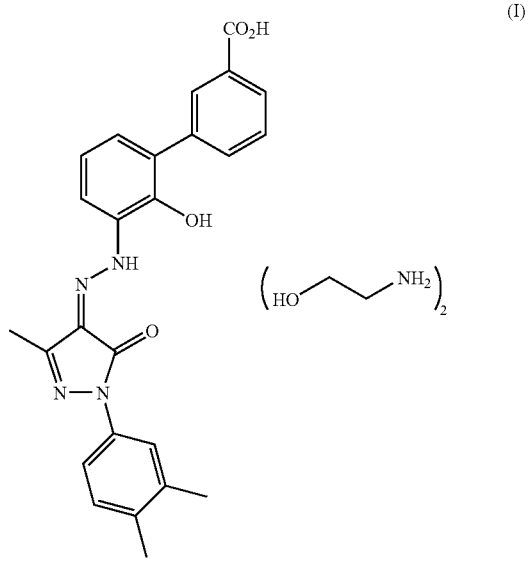

(I)

The compound of this invention is useful as an agonist of the TPO receptor, particularly in enhancing platelet production.

DETAILED DESCRIPTION OF THE INVENTION

3'-{N'-[1-(3,4-dimethylphenyl)-3-methyl-5-oxo-1,5-dihydropyrazol-4-ylidene]hydrazino}-2'-hydroxybiphenyl-3-carboxylic acid is a compound which is disclosed and claimed, along with pharmaceutically acceptable salts, hydrates, solvates and esters thereof, as being useful as an agonist of the TPO receptor, particularly in enhancing platelet production and particularly in the treatment of thrombocytopenia, in International Application No. PCT/US01/16863, having an International filing date of May 24, 2001; International Publication Number WO 01/89457 and an International Publication date of Nov. 29, 2001, the entire disclosure of which is hereby incorporated by reference.

It has now surprisingly been found that the bis-(monoethanolamine) salt of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid has numerous advantages over the free acid. The free acid is poorly soluble in water (approximately 5 micrograms per milliliter). This poor solubility adversely affects the ability of the free acid to be formulated into pharmaceutical dosage forms and reduces the bioavailability of the compound in vivo.

While the free acid is highly useful as an agonist of the TPO receptor, particularly in enhancing platelet production and particularly in the treatment of thrombocytopenia, the bis-(monoethanolamine) salt of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid has the added advantages of enhanced solubility and bioavailability.

The compound of this invention, 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine) (hereinafter—"Active Ingredient"), is useful as an agonist of the TPO receptor, particularly in enhancing platelet production and particularly in the treatment of thrombocytopenia. The Active Ingredient can be administered in a conventional dosage form prepared by combining the Active Ingredient with a conventional pharmaceutically acceptable carrier or diluent according to techniques readily known to those of skill in the art, such as those described in International Application No. PCT/US01/16863. The route of administration may be oral, parenteral or topical. The term parenteral as used herein includes intravenous, intramuscular, subcutaneous, intranasal, intrarectal, intravaginal or intraperitoneal administration. Oral administration is generally preferred.

As used herein the term "monoethanolamine" means "2-aminoethanol".

Doses of the presently invented Active Ingredient in a pharmaceutical dosage unit as described above will be an efficacious, nontoxic quantity preferably selected from the range of 0.001-100 mg/kg of total body weight, preferably 0.001-50 mg/kg. When treating a human patient in need of a TPO mimetic, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of Active Ingredient, most preferably from 0.5 to 1,000 mg of Active Ingredient. Oral administration, which uses lower dosages is preferred. Parenteral administration, at high dosages, however, also can be used when safe and convenient for the patient. The above dosages relate to the preferred amount of the Active Ingredient expressed as the free acid.

It will be recognized by one of skill in the art that the optimal quantity and spacing of individual dosages of the Active Ingredient will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the Active Ingredient given per day for a defined number of days, can be ascertained by those skilled in the art using conventional course of treatment determination tests.

Generally speaking, the compound of this invention is prepared by dissolving the free acid, 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, in an appropriate organic solvent, preferably tetrahydrofuran (hereinafter THF) or ethanol/IMS (Industrial Methylated Spirit), filtering the resultant mixture to remove contaminants, then adding this solution to a solution of two or more equivalents of ethanolamine in an organic solvent, preferably a water-miscible solvent, which may contain a measured amount of water, preferably up to 5 volumes of water with respect to the free acid. The compound of this invention is filtered off and dried, for example, dried in vacuo or air dried at an elevated temperature.

Ethanolamine, 99%, was purchased from the Aldrich Chemical Company, Milwaukee, Wis.

Tetrahydrofuran (THF) and Industrial Methylated Spirit 74 O.P. (EMS) were purchased from BDH Laboratory Supplies, Poole, England.

The following examples further illustrate the present invention. The examples are not intended to limit the scope of the invention as defined hereinabove and as claimed below.

EXAMPLE 1

Preparation of: 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid-carboxylic acid bis-(monoethanolamine)

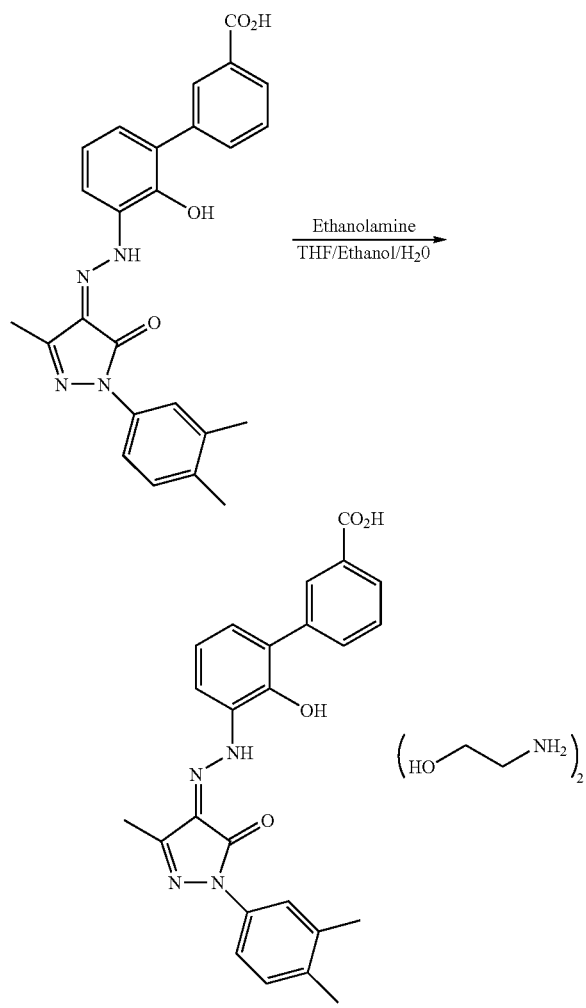

3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, 1 g of crude orange solid, in 16.75 ml of THF was stirred at approximately 30° C. Water (2.0 ml) was added slowly to maintain a temperature greater than 28° C. When the addition was complete, the temperature was returned to 30° C. and the solution filtered through a glass fibre pad (2× Whatman GFC filters) to remove particulate matter. The filter was washed through with THF (2.0 ml) which was added to the filtrate. The filtrate was allowed to cool to room temperature. Ethanolamine (0.324 g, 2.35 mol. equiv.) was dissolved in IMS (26 ml) and stirred under a nitrogen atmosphere at room temperature. The filtrate containing the free acid was added to the ethanolamine solution over 20 to 30 minutes. The resulting dark red suspension was stirred for 3 hours and the solid isolated by filtration and dried at 50° C. in a vacuum oven over night to yield 1.22 g (96%) of the title compound.

Proton NMR (400 MHz, DMSO-d6+20 ul TFA, referenced to DMSO-d5 δ 2.5): δ 2.21 (s, 3H), 2.26 (s, 3H), 2.31 (s, 3H), 2.85 (m, 4H), 3.57 (t, 4H), 7.07 (m), 7.14 (s), 7.18 (d, overlapped 3H), 7.61 (t), 7.63 (dd, overlapped 2H), ~7.7 (m, overlapped 2H), 7.79 (d), ~7.8 (br. s, overlapped 2H), 7.96 (d, 2H), 8.13 (s, 1H), 13.8 (br. s, not measurable, superimposed on TFA resonance) and signals for THF 1.76 (m) and 3.60 (overlayed by ethanolamine signal) integrating at 1.05% w/w and for ethanol 1.06 (t) and 3.44 (q) integrating at 1.3% w/w.

IR Data (Nujol mull) 1636, 1506, 1466, 1378, 1348, 1294, 1273, 1255, 1228, 1194, 1127, 1118, 1066, 1015, 767, 747 $cm^{-1}$.

EXAMPLE 2

Preparation of: 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine)

3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, 8 g of crude orange solid, was dissolved at room temperature in THF (240 ml) in a 500 ml round bottom 3-necked flask under a nitrogen atmosphere. Ethanolamine (2.2 ml, 2 molar equivalents) was added via syringe over 5 minutes. The resulting dark red suspension was stirred at room temperature for 1.5 hours and the solid isolated by filtration, washed with THF (16 ml×2) and dried at 50° C. in a vacuum oven over night to yield 10.37 g of the title compound (more than quantitative yield due to residual solvent—approximately 2.4% w/w THF as determined by NMR, otherwise similar to Example 1).

EXAMPLE 3

Preparation of: 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine)

3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid, 8 g of crude orange solid, was suspended at room temperature in ethanol (800 ml) under a nitrogen atmosphere. Ethanolamine (2.2 ml, ~2 molar equivalents) was added via syringe over 5 minutes. The resulting dark red suspension was stirred at room temperature for 45 hours and the solid isolated by filtration, washed with ethanol (10 ml×2) and dried at 50° C. in a vacuum oven over night to yield 9.83 g (96% yield) of the title compound. NMR similar to Example 1; ethanol content 1.3% w/w but no THF present.

EXAMPLE 4

Preparation of: 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine)

3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid (259.0 g) was stirred in THF (4660 ml) at room temperature until completely dissolved. The solution was filtered and the reactor washed with more THF (520 ml) via the filter. (Combined filtrate=Solution 1).

Meanwhile, another reactor was set up for atmospheric distillation with overhead stirring. The reactor was charged in turn with IMS 74 O.P. (7770 ml) and then ethanolamine (354 ml). The solution was stirred vigorously and heated until the contents started to distil (BP. 76-77° C.).

Solution 1 was transferred to the dropping funnel fitted to this reactor. When the contents of the reactor were distilling at a constant rate (ca. 50 ml distillate collected), Solution 1 was added from the dropping funnel at about the same rate or slightly slower than the distillation rate. On completion of the addition the dropping funnel was washed through with IMS (260 ml×2) ensuring that all the free acid was washed into the reaction mixture. The apparatus was rearranged for reflux and the resulting dark red suspension stirred at reflux under nitrogen for 30 minutes. It was allowed to cool slowly (overnight) to room temperature (ca. 20° C.) with stirring under nitrogen.

The suspension was filtered and the dark purple solid washed on the filter with IMS (520 ml×2). It was vacuum dried at room temperature, then dried at 50° C. in a vacuum oven over night. Weight yield=323.9 g, 98%. Residual solvents (GCS) THF=<0.05%, ethanol=0.12%.

The title compound displayed NMR and IR spectra essentially as indicated in Example 1 with only traces of solvent present.

EXAMPLE 5

Relative Solubilities

The solubility of 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid as the free acid (Compound A) and as the bis-(monoethanolamine) salt (Compound B) was determined in three different systems: water, 0.1 HCl and methanol. The data are summarized in Table 1 below.

TABLE 1

| Solvent<br>Solubility at 25 deg | Compound A mg/ml<br>mg/ml | Compound B mg/ml<br>mg/ml |
| --- | --- | --- |
| Water | <0.001 | 14.2 |
| 0.1% HCl | <0.001 | <0.001 |
| methanol | 1.9 | 6.4 |

The present invention includes within its scope pharmaceutical compositions comprising 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine), as the active ingredient, in association with a pharmaceutically acceptable carrier or diluent. The compound of this invention can be administered by oral or parenteral routes of administration and can be formulated in dosage forms appropriate for each route of administration including capsules, tablets, pills, powders and granules. In such solid dosage forms, the active compound is admixed with at least one inert diluent. The oral dosage forms can also comprise, as is normal practice, additional substances other than inert diluents, e.g., lubricating agents, glidants and antioxidants. In the case of capsules, tablets and pills, the dosage forms may also comprise buffering agents. Tablets and pills can additionally be prepared for a sustained release.

Preparations according to this invention for parenteral administration include sterile aqueous solutions although nonaqueous suspensions of emulsions can be employed. Such dosage forms may also contain adjuvants such as preserving, wetting, osmotic, buffering, emulsifying and dispersing agents. They may be sterilized by, for example, filtration through a bacteria retaining filter, by incorporating sterilizing agents into the compositions, irradiating the compositions or by heating the compositions.

The following examples further illustrate the pharmaceutical compositions which are a feature of this invention.

EXAMPLE 6

Tablet Composition

Lactose, microcrystalline cellulose, sodium starch glycolate, magnesium stearate and 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine) are blended in the proportions shown in Table 2 below. The blend is then compressed into tablets.

TABLE 2

| INGREDIENT | mg. |
| --- | --- |
| 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine) | 8.45 |
| microcrystalline cellulose | 112 |
| lactose | 70 |
| sodium starch glycolate | 8 |
| magnesium stearate | 2 |

EXAMPLE 7

Injectable Parenteral Composition

An injectable form for administering 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine) is produced by stirring 5.0 mg. of the compound in 1.0 ml. of normal saline.

While the preferred embodiments of the invention are illustrated by the above, it is to be understood that the invention is not limited to the precise instructions herein disclosed and that the right to all modifications coming within the scope of the following claims is reserved.

What is claimed is:

1. A method of enhancing platelet production in a human in need thereof which comprises administering to such human an effective amount of the compound 3'-[(2Z)-[1-(3,4-dimethylphenyl)-1,5-dihydro-3-methyl-5-oxo-4H-pyrazol-4-ylidene]hydrazino]-2'-hydroxy-[1,1'-biphenyl]-3-carboxylic acid bis-(monoethanolamine).

2. The method of claim 1 wherein the compound is administered orally.

3. The method of claim 1 wherein the compound is administered parenterally.

* * * * *